US007122208B2

(12) United States Patent
Bolton et al.

(10) Patent No.: US 7,122,208 B2
(45) Date of Patent: Oct. 17, 2006

(54) COMPOSITIONS CONTAINING APOPTOTIC ENTITIES (75) Inventors: Anthony E. Bolton, Tideswell (GB); Arkady Mandel, North York (CA)

(73) Assignee: Vasogen Ireland Limited, (IE)

( * ) Notice: Subject to any disclaimer, the term of this patent is extended or adjusted under 35 U.S.C. 154(b) by 453 days.

(21) Appl. No.: 10/115,943

(22) Filed: Apr. 5, 2002

(65) Prior Publication Data

US 2002/0155098 A1 Oct. 24, 2002

Related U.S. Application Data (60) Provisional application No. 60/282,120, filed on Apr. 6, 2001.

(51) Int. Cl.
*A61K 35/14* (2006.01)
(52) U.S. Cl. ............... 424/529; 424/93.7; 435/2; 435/366; 435/372
(58) Field of Classification Search ............... 424/529, 424/93.7; 435/2, 366, 372
See application file for complete search history.

(56) References Cited

U.S. PATENT DOCUMENTS

| 5,834,030 | A | | 11/1998 | Bolton |
| 5,980,954 | A | * | 11/1999 | Bolton ............... 424/613 |
| 6,086,552 | A | | 7/2000 | Bolton |

FOREIGN PATENT DOCUMENTS

| WO | 96/34613 | 11/1996 |
| WO | 00/41705 | 7/2000 |

OTHER PUBLICATIONS

Kuljis et al., Minimal Cognitive Impairment, http://www.emedicine.com/neuro/topic714.htm, last updated Jun. 18, 2004.*
Mecocci, Journal of Alzheimer's Disease 6: 159-163 (2004).*
Malfroy et al., Cellular Immunology 177: 62-68 (1997).*
Bliss TV, Collingridge GL. "A synaptic model of memory: long-term potentiation in the hippocampus." Nature. 361(6407):31-9 (1993).
Bradford MM. "A rapid and sensitive method for the quantitation of microgram quantities of protein utilizing the principle of protein-dye binding." Anal Biochem. 72:248-54 (1976).
Green LN. "Corticosteroids in the treatment of Sydenham's chorea." Arch. Neurol. 35(1): 53-4 (1978).
Haan EA, et al. "Protection of neocortical tissue prisms from freeze-thaw injury by dimethyl sulphoxide," J. Neurochem. 37(1):243-6 (1981).
Kedziora J, et al. "Down's syndrome: a pathology involving the lack of balance of reactive oxygen species." Free Radic. Biol. Med.. 4(5): 317-30 (1988).
Kouamé N, et al. "Vasocare-therapy attenuates telemetered temperature responses to stress in SHR." 9th International Symposium on SHR and Cardiovascular Genetics, Montreal, Canada, #P-136, Nov. 13-16, 1997. (abstract).
Layton ME, et al. "Reactive oxidant species in piriform cortex extracellular fluid during seizures induced by systemic kainic acid in rats." J. Mol. Neurosci 13(1-2): 63-8 (1999).
Lebel CP, et al. "Evaluation of the probe 2',7'-dichlorofluorescin as an indicator of reactive oxygen species formation and oxidative stress." Chem Res Toxicol. 5(2):227-31 (1992).
Maroney AC, et al. "Motoneuron apoptosis is blocked by CEP-1347 (KT 7515), a novel inhibitor of the JNK signaling pathway." J Neurosci. 18(1):104-11 (1998).
Martin DSD, et al. "A diet enriched in a-lipoic acid reverses the age-related compromise in antioxidant defenses in rat cortical tissue." Nutritional Neuroscience 3: 193-206 (2000).
Mcgahon B, et al. "The synergism between metabotropic glutamate receptor activation and arachidonic acid on glutamate release is occluded by induction of long-term potentation in the dentate gyrus." Neuroscience. 72(3):847-55 (1996).
Mogi M, et al. "Interleukin (IL)-1b, IL-2, IL-4, IL-6 and transforming growth factor-a levels are elevated in ventricular cerebrospinal fluid in juvenile parkinsonism and Parkinson's disease." Neurosci Lett. 211(1):13-6 (1996).
Murray CA, et al. "Evidence that increased hippocampal expression of the cytokine interleukin-1b is a common trigger for age- and stress-induced impairments in long-term potentiation." J Neurosci. 18(8):2974-81 (1998).
O'Donnell E, et al. "Age-related impairment in LTP is accompanied by enhanced activity of stress-activated protein kinases: analysis of underlying mechanisms." Eur J Neurosci. 12(1):345-52 (2000).
Park DS, et al. "Ordering the cell death pathway. Differential effects of BCL2, an interleukin-1-converting enzyme family protease inhibitor, and other survival agents on JNK activation in serum/nerve growth factor-deprived PC12 cells." J Biol Chem. 271(36):21898-905 (1996).
Rabinovitch BA, et al. "VasoCare™ PSCT normalizes the Th2 cell subset in scleroderma." XII Pan-American Congress of Rheumatology, Montreal, Canada, 1998.
Schuchmann S, et al. "Increased mitochondrial superoxide generation in neurons from trisomy 16 mice: a model of Down's syndrome." Free Radic. Biol. Med. 28(2): 235-50 (2000).
Shivji GM, et al. "The effect of VAS972 on allergic contact hypersensitivity." J Cutan Med Surg. 4(3):132-7 (2000).
Tenneti L, et al. "Role of caspases in N-methyl-D-aspartate-induced apoptosis in cerebrocortical neurons." J Neurochem. 71(3):946-59 (1998).
Trembovler V , et al. "Antioxidants attenuate acute toxicity of tumor necrosis factor-alpha induced by brain injury in rat." J. Interferon Cytokine Res. 19(7): 791-5 (1999).
Vereker E, et al. "Lipopolysaccharide inhibits long term potentiation in the rat dentate gyrus by activating caspase-1." J Biol Chem. 275(34):26252-8 (2000).

(Continued)

Primary Examiner—Jean C. Witz
(74) Attorney, Agent, or Firm—Foley & Lardner LLP (57) ABSTRACT Disclosed are methods for treating and preventing neurological disorders which have a significant inflammatory component. The methods of the present invention involve extracting blood from a patient, subjecting the blood ex vivo to at least one stressor selected from the group consisting of an oxidative environment, thermal stress and UV light, and then re-administering the blood to the patient, thereby reducing inflammation.

28 Claims, 4 Drawing Sheets

OTHER PUBLICATIONS

Vereker E, et al. "The inhibitory effect of interleukin-1b on long-term potentiation is coupled with increased activity of stress-activated protein kinases." *J Neurosci.* 20(18):6811-9 (2000).

Wildburger R, et al. "Post-traumatic dynamic changes in the antibody titer against oxidized low density lipoproteins." *Wien Klin Wochenshr.* 112(18) 798-803 (2000).

Database Medline [Online] US National Library of Medicine (NLM), Bethesda, MD, US; 1998, Sagara Y: "Cellular mechanisms of resistance to oxidative stress," Database accession No. NLM9641255.

Database Medline [Online] US National Library of Medicine (NLM), Bethesda, MD, US; 1995, Rogers J: "Inflammation as a pathogenic mechanism in Alzheimer's disease," Database accession No. NLM7763341.

Database Medline [Online] US National Library of Medicne (NLM), Bethesda, MD, US; 1999, Hirsch E C: "Mechanism and consequences of nerve cell death in Parkinson's disease," Database accession No. NLM10370907.

Database Medline [Online] US National Library of Medicine (NLM), Bethesda, MD, US; 2003, Beal M F: "Mitochondria, oxidative damage and inflammationin Parkinson's disease," Database accession No. NLM12846981.

* cited by examiner

COMPOSITIONS CONTAINING APOPTOTIC ENTITIES

REFERENCE TO RELATED APPLICATIONS

This application is based upon and claims priority from U.S. provisional patent application serial No. 60/282,120 filed Apr. 6, 2001, the disclosure of which is incorporated herein by reference, in its entirety.

BACKGROUND OF THE INVENTION

1. Field of the Invention

This invention is directed to methods for treating the inflammatory component of brain disorders in mammalian patients, and more particularly for treating those neurological brain disorders in which reactive oxygen species play a significant role in the underlying inflammatory pathology.

2. State of the Art

The events that lead to neurological disorders with a significant inflammatory component (including myasthenia gravis, GBS, CIDP, and multiple sclerosis) are not clear, but the following sequential steps appear to be critical. (1) The breaking of tolerance, a process in which cytokines, molecular mimicry, or superantigens may play a role in rendering previously anergic T-cells to recognize neural autoantigens. (2) Antigen recognition by the T-cell receptor complex and processing of the antigen via the major histocompatibility complex class I or II. (3) Costimulatory factors, especially B7 and B7-binding proteins (CD28, CTLA-4) and intercellular adhesion molecule (ICAM-1) and its leukocyte function-associated (LFA)-1 ligand. (4) Traffic of the activated T cells across the blood-brain or blood-nerve barrier via a series of adhesion molecules that include selectins, leukocyte integrins (LFA-1, Mac-1, very late activating antigen (VLA)-4) and their counterreceptors (ICAM-1, vascular cell adhesion molecule (VCAM)) on the endothelial cells. (5) Tissue injury when the activated T cells, macrophages, or specific autoantibodies find their antigenic targets on glial cells, myelin, axon, calcium channels, or muscle.

In designing specific immunotherapy, the main components involved in every step of the immune response need to be considered. Targets for specific therapy in neurological disease include agents and treatments that (a) interfere or compete with antigen recognition or stimulation; (b) inhibit costimulatory signals or cytokines; (c) inhibit the traffic of the activated cells to tissues; and (d) intervene at the antigen recognition sites in the targeted organ.

Reactive oxygen species (ROS) are activated forms of oxygen, including superoxide anion ($O_2.^-$) and hydroxyl radicals (HO.) together with hydrogen peroxide ($H_2O_2$) and various unstable intermediates of lipid peroxidation. They are generated as a result of aerobic metabolism. Neuronal brain tissue is particularly susceptible to oxidative damage due its to high consumption of oxygen and its limited antioxidant defense system. Reactive oxygen species formation is thought to have an impact on synaptic plasticity, cell signaling and the aging process. An age-related increase in reactive oxygen species production has been demonstrated (Martin et al., 2000) and the accumulation of reactive oxygen species has also been shown to be increased in the hippocampus as a consequence of peripheral LPS administration (Vereker et al., 2000a). This is mimicked by IL-1β administration (Vereker et al., 2000b). O'Donnell and colleagues (2000) have reported parallel changes in reactive oxygen species formation and IL-1β production; reactive oxygen species formation was shown to cause an increase in IL-1β production while IL-1β has the ability to induce reactive oxygen species formation thus suggesting the existence of a positive feedback loop which is potentially damaging to cells.

Increased concentrations of IL-1β have also been closely linked with neuronal degeneration (Mogi et al., 1996; Tenneti et al., 1998).

Enhanced activity of the stress-activated kinase c-Jun $NH_2$-terminal kinase (JNK) is associated with cell degeneration and death (Park et.al., 1996; Maroney et.al., 1998), and has been shown to be activated in the hippocampus by several agents, including hydrogen peroxide, an inducer of reactive oxygen species production, and pro-inflammatory cytokines.

Another example of a neuronal brain deficit induced by IL-1β and LPS, is the impairment of long term potentiation (LTP) in the hippocampus (Vereker et al 2000a; Murray & Lynch, 1998). LTP is a form of synaptic plasticity that was originally described in the hippocampus, a brain region that is particularly vulnerable to degeneration which is associated with cognitive dysfunction. On the basis of this and other observations, LTP has been proposed as a biological substrate for learning and memory (Bliss & Collingridge, 1993).

Certain neurological brain disorders such as Downs syndrome (Layton et.al., Kedziora et.al., Schuchmann et. al.), epilepsy, brain trauma (e.g. physical damage to the brain such as concussion)(Layton et. al., Wildburgur et. al., Trembovler et. al.) and Huntington's disease (chorea)(Green) are currently understood to involve inflammation of brain cells as a significant component of the underlying pathology of the disorder. This inflammation could be the consequence of one or more of a variety of biological processes, such as the generation of excess-amounts of inflammatory cytokines such as IL-1β and TNF-α, in the brain cells or other components of the brain tissue, perhaps associated with the presence of high concentrations of reactive oxygen species in the brain tissue, which correlates to high levels of tissue damage or exacerbation of the disease. Reactive oxygen species are one of the effectors of inflammation in tissue such as brain tissue.

Other neurological disorders which have a significant inflammatory component include Guillain-Barré syndrome (GBS), chronic inflammatory demyelinating polyneuropathy (CIDP), myasthenia gravis (MG), dermatomyositis, polymyositis, inclusion body myositis, post stroke, neurosarcoidosis, vascular dementia, closed head trauma, vasospasm, subarachnoid hemorrhage, adrenal leukocytic dystrophy (storage disorders), inclusion body dermatomyostis, minimal cognitive impairment and duchenne muscular dystrophy.

Chronic inflammatory demyelinating polyneuropathy (CIDP) is a neurological disorder characterized by slowly progressive weakness and sensory dysfunction of the legs and arms. The disorder, which is sometimes called chronic relapsing polyneuropathy, is caused by damage to the myelin sheath of the peripheral nerves. CIDP can occur at any age and in both genders, is more common in young adults, and in men more so than women. The primary symptoms include slowly progressive muscle weakness and sensory dysfunction affecting the upper and lower extremities. Other symptoms may include fatigue; abnormal sensations including burning, numbness and/or tingling sensations (beginning in the toes and fingers); paralysis of the arms and/or legs; weakened or absent deep tendon reflexes (areflexia); and, aching pain affecting various muscle groups.

CIDP is closely related to the more common, acute demyelinating neuropathy known as Guillain-Barré syndrome (GBS). CIPD is considered the chronic counterpart of the acute disease GBS. CIDP is distinguished from GBS, chiefly by clinical course and prognosis. However, both disorders have similar clinical features, and both share the CSF albuminocytological dissociation and the pathological abnormalities of multi-focal inflammatory segmental demyelination with associated nerve conduction features reflecting demyelination.

Guilain-Barré Syndrome (GBS) is an acute predominately motor polyneuropathy with spontaneous recovery that may lead to severe quadriparesis and requires artificial ventilation in 20–30% of patients. The diseases that underlie this syndrome have been classified as acute inflammatory demyelinating polyneuropathy (AIDP), the most common form, acute motor and sensory axonal neuropathy (AMSAN), and acute motor axonal neuropathy (AMAN). Fisher syndrome is a cranial nerve variant of GBS which characteristically results in opthalmoplegia, ataxia and areflexia. GBS is often preceded by infection with either *Campylobacter jejuni*, which is most common, cytomegalovirus (CMV), Epstein-Barr virus or *Mycoplasma pneumoniae*.

Autoimmune myasthenia gravis (MG) is a disorder of neuromuscular transmission leading to fluctuating weakness and abnormal fatigueability. Weakness is attributed to the blockade of acetylcholine receptors (AChRs) at the neuromuscular endplate by circulating autoantibodies, followed by local complement activation and destruction of acetylcholine receptors (Stangel et al, *J. Neurol. Sci.* 153(2): 203–14 (1998)). AchR is expressed on regenerating myoblasts but in normal adult muscle the AChR is only expressed at the motor endplate. In patients with early onset MG however the thymic medulla is infiltrated by lymph node-like T cells and germinal centres and there are myoblast-like myoid cells in the thymic medulla which express AChR. Therefore the presentation of the AChR antigen by these cells or by myoblasts is likely to be involved in the disease process (Curnow et al, *J. Neuroimmunol.* 115(1–2): 127–134 (2001)). In studies of experimental autoimmune myasthenia gravis (EAMG) the Th1 cytokine, INF-$\gamma$, has been shown to be involved in disease progression and has been reported to be capable of inducing the production by myoblasts of class I and II major histocompatibility antigens, AChR and ICAM-1. IL-1 has also been shown to play a role in EAMG where disruption of the IL-1 beta gene was shown to diminish acetylcholine receptor-induced responses (Garcia et al, *J. Neuroimmunol* 120(1–2):103–11 (2001); Stegall et al, *J. Neuroimmunol.* 119(2):377–386 (2001)).

The causes of inflammatory muscle diseases dermatomyositis, polymyositis and inclusion body myositis (IBM) are unknown, but immune mechanisms are strongly implicated. Although clinically and immunopathologically distinct, these diseases share three dominant histological features: inflammation, fibrosis and loss of muscle fibres. In dermatomyositis, the endomysial inflammation and muscle fiber destruction is preceded by activation of the complement system of plasma proteins, and deposition of membranolytic attack complex on the endomysial capillaries (Dalakas, *Curr. Opin. Pharmacol.* 1(3):300–306 (2001)). There is evidence that this attack may also involve the blood vessels in the dermis (Dalakas et al, *Curr. Opin. Pharmacol.* 9(3): 235–239 (1996)). Transforming growth factor beta, shown to be overexpressed in the perimysial connective tissue in dermatomyositis, is down-regulated after successful immunotherapy and reduction of inflammation and fibrosis (Dalakas, *Arch. Neurol.* 55(12):1509–1512 (1998)).

In polymyositis and IBM the disease begins with the activation of $CD8^+$ T cells. These cytotoxic T cells reach the endomysial parenchyma to recognise muscle antigen(s) associated with the upregulation of the major histocompatibility complex (MHC) I on muscle fibres. The autoinvasive T cells exhibit gene rearrangement of their T-cell receptors (TCR) and are specifically selected and clonally expanded in situ by heretofore previously unknown antigens. Muscle cells do not normally express MHC I and II but in cases of polymyositis and IBM over expression of MHC is an early event that can be detected even in areas remote from the inflammation. INF$\gamma$ and TNF$\alpha$, cytokines that induce MHC, have been found in patients with active polymyositis (Dalakas, *Curr. Opin. Pharmacol.* 1(3):300–306 (2001)).

No signs of apoptosis have been detected in patients with inflammatory myopathies and in fact two strong anti-apoptotic molecules have recently been found to be expressed in the muscle fibers. One is the Fas-associated death domain-like IL-1-converting enzyme inhibitory protein (FLIP) and the other human IAP (inhibitor of apoptosis protein)-like protein. The result of unsuccessful apoptotic clearance of inflammatory cells is likely to be the cause of the sustained chronic cytotoxic muscle fiber damage (Vattemi et al, *J. Neuroimmunol.* 111(1–2):146–151 (2000)).

Sarcoidosis is a multisystem chronic disorder with unknown cause and a worldwide distribution. Neurosarcoidosis is a complication of sarcoidosis involving inflammation and abnormal deposits in the tissues of the nervous system. Sudden, transient facial palsy is common with involvement of cranial nerve VII. Other manifestations include aseptic meningitis, hydrocephalus, parenchymatous disease of the central nervous system, peripheral neuropathy and myopathy. Intracranial sarcoid may mimic various forms of meningitis, including carcinomatous and intracranial mass lesions such as meningioma, lymphoma and glioma, based on neuroradiological imaging. A lumbar puncture may show signs of inflammation. Elevated levels of angiotensin converting enzyme may be found in the blood or CSF. Therapy consists of immunosuppressive agents and corticosteroids (Nowak et al, *J. Neurol.* 248(5):363–372 (2001); Stern et al, *Arch. Neurol.* 42(9):909–917 (1985)).

Vascular dementia (VaD) is the general term for dementia caused by organic lesions of vascular origin, such as cerebral infarction, intracerebral haemorrhage or ischemic changes in subcortical white matter. It is the most frequent cause of dementia after AD accounting for about 20% of cases and 50% in subjects over 80 years (Dib, *Arch. Gerontol. Geriatr.* 33(1):71–80 (2001); Parnetti et al, *Int. J. Clin. Lab Res.* 24(1):15–22 (1994)). The clinical distinction between AD and VaD may be difficult and there are standard guidelines for research studies. VaD and AD can co-exist as "mixed dementia" where the presence of cerebrovascular disease may worsen Alzheimer dementia. Traditionally AD is characterized by the insidious onset of memory loss, followed by a gradual progression to dementia in the face of normal findings on neurological examination. VaD on the other hand, is characterized by stepwise cognitive decline punctuated by episodes of stroke that are accompanied by focal deficits on neurological examination, and evidence of stroke on computed topography (CI) or magnetic-resonance imaging (Jagust, *Lancet* 358(9299):2097–2098 (2001)). It is assumed that the risk factors for stroke and vascular disease are also factors for VaD. These include hypertension, smoking, diabetes, obesity, cardiac rhythm disorders, hyperlipidaemia, hypercholesterolaemia and hyperhomocystein-aemia. The apolipoprotein E4 genotype is also considered as a risk factor for VaD, AD and ischemic stroke (Dib, *Arch.*

Gerontol. Geriatr. 33(1):71–80 (2001)). Current treatments of vascular dementia include anti-platelet agents and/or surgery, and the treatment of cognitive symptoms (Parnetti et al, *Int. J. Clin. Lab. Rews.* 24(1):15–22 (1994)).

Head trauma is associated with a variety of physiological and cellular phenomena such as ischemia, increased permeability of the blood-brain barrier (BBB), edema, necrosis and motor and memory dysfunction (Moor et al, *Neurosci. Lett.* 316(3):169–172 (2001); Shohami et al, *J. Neuroimmunol.* 72(2):169–177 (1997)). Ischemia caused by the initial brain injury induces a cascade of secondary events and the release of excitatory amino acids (EAA) such as glutamate and aspartate. Alteration in the levels of ions and neuromodulators lead to oxidation and cellular membrane damage and ultimately cellular death (Stahel et al, *Brain Res. Rev.* 27(3):243–256 (1998)). Experimental models for closed head injury (CHI) developed in the rat show the spatial and temporal induction of IL-1, IL-6 and TNF-α gene mRNA transcription along with an induction of IL-6 and TNF-α activity in the rat brain (Shohami et al, *J. Neuroimmunol.* 72(2):169–177 (1997)). IL-1β has also been shown to be released and it is the presence of these cytokines along with damage to endothelial cells that result in disruption of the BBB integrity. This disruption allows the recruitment of neutrophils into the subarachnoid space (Stahel et al (1998)).

TNF-α has been identified in the brain in several pathological conditions and inhibitors of TNF-α such as dexanabinol (HU-211) have been shown to improve neurological outcome following CHI (Shohami et al, *J. Neuroimmunol.* 72(2):169–177 (1997)).

Cerebral vasospasm is delayed onset cerebral artery narrowing in response to blood clots left in the subarachnoid space after spontaneous aneurysmal subarachnoid hemorrhage (SAH) (Ogihara et al, *Brain Res.* 889(1–2):89–97 (2001)). It is angiographically characterized as the persistent luminal narrowing of the major extraparenchymal cerebral arteries and affects the cerebral microcirculation and causes decreased cerebral blood flow (CBF) and delayed ischemic neurological deficits. A number of studies have demonstrated morphological changes in cerebral arteries after SAH. Smooth muscle cells showed necrotic changes, such as dense bodies, degeneration of mitochondria, condensed lysosomes and dissolution of nuclear substances and the appearance of cell debris (Sobey et al, *Clin. Exp. Pharmacol. Physiol.* 25(11):867–876 (1998)). The impaired dilator and increased constrictor mechanisms that occur after SAH may be caused by oxyhaemoglobin produced by erythrocytes that inactivates NO in the subarachnoid space. Alternatively it may be due to an impaired activity of soluble guanylate cyclase resulting in reduced basal levels of cGMP in cerebral vessels and so a reduced responsiveness to NO (Ogihara et al, *Brain Res.* 889(1–2):89–97 (2001)). Production of IL-6 and IL-8 in the cerebrospinal fluid following SAH has also been demonstrated. It is thought that IL-6 may play a particular role in vasospasm as in induced vasoconstriction in a canine cerebral artery (Osuka et al, *Acta Neurochir* 140(9):943–951 (1998)).

Duchenne muscular dystrophy (DMD) is one of the most common, inherited, lethal disorders in childhood. It is an X-linked neuromuscular disease that affects 1 in 3500 males. Progressive muscle weakness begins between 2 and 5 years of age and ultimately leads to premature death by respiratory or cardiac failure during the middle to late twenties. Approximately 30% of cases are due to spontaneous mutation of the dystrophin genes while the remainder are inherited (Spencer et al, *Neuromuscul. Disord.* 11(6–7):556–564 (2001)). DMD patients therefore lack the protein dystrophin which is an essential link in the complex of proteins that connect the cytoskeleton to the extracellular matrix (Alderton et al, *Trends Cardiovascular Med.* 10(6):268–272 (2000)). Although gene therapy is the only cure for DMD it is believed that immune interventions may slow the progress of the disease. The reason for this is that there is evidence that immune cell interactions with dystrophin-deficient muscle can contribute to cell death in dystrophinopathies. It has also been shown that the population of immune cells in dystrophic muscle are not only different from those found that invade mechanically-damaged tissue; they are similar to those found in inflammatory disease such as polymyositis. Current research indicates that T cells may play a role in the pathology of dystrophin deficiency and that there may be an autoimmune component to the disease in which T cells are activated by a common antigen (Spencer et al, *Neuromuscular Disord.* 11(6–7):556–564 (2001)).

U.S. Pat. No. 5,834,030 (Bolton) describes a process for treating a patient to combat peripheral vascular disease, which comprises extracting an aliquot of the patient's blood, treating the blood aliquot extracorporeally with stressors such as an oxidative environment (ozone/oxygen gas mixture bubbled there through), incident UV light and an elevated temperature.

U.S. Pat. No. 5,980,954 (Bolton) describes similar processes for treating autoimmune diseases in mammalian patients.

It is an object of the present invention to provide a novel treatment or prophylaxis of neurological disorders which have a significant inflammatory component, such as chronic inflammatory demyelinating polyneuropathy and Guillain-Barré syndrome.

"Immune modulation therapy" as the term is used herein, is an ex vivo treatment protocol which involves exposure of autologous peripheral blood to combinations of at least two physicochemical stressors, namely heat, oxidative stress such as ozonation and electromagnetic radiation such as ultraviolet irradiation and subsequent administration of the treated blood to the patient, suitably by intramuscular injection. There is recent evidence that such immune modulation therapy suppresses contact hypersensitivity (Shivji et al., 2000) as well as demonstrating an attenuated hyperthermic response to immobilisation stress in spontaneously hypertensive rats (Kouamé et al., 1997) thus suggesting a possible protective role. In support of this is the report that following such immune modulation therapy a reduction in the relative number of pro-inflammatory TH1 cells and an increase in TH2 cells have been observed in humans, signifying a reduction in the inflammatory response (Rabinovitch et al., 1998).

SUMMARY OF THE INVENTION

This invention is directed to the surprising and unexpected discovery that such immune modulation therapy can exert beneficial anti-inflammatory effects across the blood-brain barrier of a mammalian patient, apparently through a significant reduction of the accumulation of reactive oxygen species and/or a significant down-regulation of associated inflammatory cytokines such as TNF-α, particularly in the cortical tissue of mammals. Accordingly, the therapy is suitable for either prophylactic or therapeutic treatment of the inflammatory component of neurological brain diseases such as Downs syndrome, epilepsy, Huntington's disease and brain traumas, through mediation of the development or activity of reactive oxygen species which play a role in the development or manifestation of such inflammation.

The present invention also provides for a method for the prophylactic or therapeutic treatment of inflammatory components and inflammatory aspects of a neurological disease in a mammalian patient diagnosed with or at risk of a neurological disease, which method comprises:

administering to said patient an aliquot of blood which has been treated ex vivo with at least two stressors selected from the group consisting of an oxidative environment, thermal stress and electromagnetic radiation, wherein the concentration of the reactive oxygen species in neuronal cells or tissues of said patient is reduced, with associated reduction of harmful inflammatory effects therein.

From another aspect, the present invention provides a process for alleviating the symptoms of a neurological brain disorder having a significant inflammatory component associated with excess active oxygen species (reactive oxygen species and oxidative free radicals), such as Down's syndrome, Huntington's disease, epilepsy and brain traumas, which comprises scavenging of active oxygen species from the brain of a mammalian patient by administering to said patient an aliquot of blood which has been treated ex vivo with at least two stressors selected from the group consisting of an oxidative environment, thermal stress and electromagnetic radiation.

Accordingly, the present invention is also a method of alleviation, prophylaxis against or preconditioning to hinder the onset and progression of neurodisorders which have a significant inflammatory component, such as Guillain-Barré syndrome (GBS), chronic inflammatory demyelinating polyneuropathy (CIDP), myasthenia gravis (MG), dermatomyositis, polymyositis, inclusion body myositis, post stroke, neurosarcoidosis, vascular dementia, closed head trauma, vasospasm, subarachnoid hemorrhage, adrenal leukocytic dystrophy (storage disorders), inclusion body dermatomyostis, minimal cognitive impairment and duchenne muscular dystrophy, wherein said method comprises treating a patient suffering from or at risk to contract such a disorder and having impaired endothelial function at the blood vessels, to improve the performance of endothelial function at the blood-brain barrier or at the blood-nerve barrier towards restoration of normal endothelial function. This represents a novel and innovative approach to the management and treatment of neurological disorders.

BRIEF DESCRIPTION OF THE DRAWINGS

In the accompanying drawing:

FIG. 1 is a graphical presentation of the effect of the treatment according to a preferred embodiment of the invention on the body weight of test animals, as described in the specific experimental section below. VasoCare™ therapy does not significantly alter body weight (FIG. 1a) or dose of urethane administered to induce anaesthesia (FIG. 1b) but there is an increase in the amplitude required to induce an action potential (FIG. 1c). Data is expressed as means with standard errors.

THE PREFERRED EMBODIMENTS

In one of the preferred methods of this invention, a patient having a neurological disease condition with a significant inflammatory component mediated by reactive oxygen species, or at risk of developing such a brain disease condition, is first identified. Such patient may have a risk which is significantly greater than the risk in the average population, e.g. as a result of prior trauma, hereditary indication and the like. That patient is then evaluated to determine whether that disease condition or risk of disease condition can be effectively treated by reducing the concentration of reactive oxygen species. If in the opinion of the attending clinician, a reduction in the concentration of reactive oxygen species and associated reduction in neurological inflammation would be suitable for the prophylactic or therapeutic treatment of such a neurological disease, Immune modulation therapy is administered to said patient.

Accordingly, in one of its preferred aspects, this invention is directed to a method for the prophylactic or therapeutic treatment of the inflammation-associated aspects of a neurological disease having a significant inflammatory component and mediated at least in part by reactive oxygen species, which method comprises:

(a) identifying a patient having a neurological brain disease condition or at risk of developing a neurological brain disease condition having a significant inflammatory component and mediated by reactive oxygen species;

(b) evaluating the patient identified in (a) above to determine whether that disease condition or risk of disease condition can be effectively treated by reducing the concentration of reactive oxygen species; and (c) if a reduction in the concentration of reactive oxygen species would be suitable for the prophylactic or therapeutic treatment of such a disease, then (d) administering to said patient an aliquot of blood which has been treated ex vivo with at least two stressors selected from the group consisting of an oxidative environment, thermal stress and electromagnetic radiation, wherein, following such administration, the neurological brain tissue inflammation and/or the concentration of the reactive oxygen species in the neurological brain tissue of said patient is reduced.

The patient is a mammal and preferably a human.

The aliquot of blood is treated by being subjected to stressors which have been found to modify the blood. According to the present invention, the blood aliquot can be modified by subjecting the blood, or separated cellular or non-cellular fractions of the blood, or mixtures of the separated cells and/or non-cellular fractions of the blood, to stressors selected from temperature stressors, electromagnetic emissions and oxidative environments, or any combination of such stressors, simultaneously or sequentially.

DETAILED DESCRIPTION OF THE INVENTION

The following terms are defined with respect to this invention:

"Therapeutic treatment" refers to the treatment of a disease wherein the treatment reduces or eliminates the symptoms of that disease.

"Prophylactic treatment" or "prophylaxis" refers to the prevention or hindrance of development of disease.

The terms "aliquot," "aliquot of blood" or similar terms used herein include whole blood, separated cellular fractions of the blood including platelets, separated non-cellular fractions of the blood including plasma, and combinations thereof.

Methodology

The method of this invention provides for the prophylactic or therapeutic treatment of a neurological brain disease mediated by reactive oxygen species. In this method a patient is first identified as having such a disease condition or is at risk of having such a disease condition mediated by reactive oxygen species. The patient is then evaluated to determine whether that disease condition or risk of disease condition can be effectively treated by reducing the concentration of reactive oxygen species. Such evaluation is made by the attending clinician based upon the disease to be treated and the progression of the disease. Such factors are well within the skill of the art. If, in the opinion of the attending clinician, a reduction in the concentration of reactive oxygen species would be suitable for the prophylactic or therapeutic treatment of such a disease, then the patient is administered an aliquot of blood which has been treated ex vivo with at least two stressors selected from the group consisting of an oxidative environment, thermal stress and electromagnetic radiation. The ex vivo treatment of the aliquot of blood is described below. The method provides a reduced concentration of the reactive oxygen species in said patient.

In this preferred method, the patient is evaluated to determine whether the neurological brain disease condition or risk of neurological brain disease condition could be effectively treated by reducing the concentration of reactive oxygen species, e.g. whether its inflammation component associated with the presence of reactive oxygen species can be effectively reduced by reducing the concentration of reactive oxygen species. In this regard, the reduction of the reactive oxygen species is reduced in the patient at the time when a reduction of reactive oxygen species effectively treats (either prophylactically or therapeutically) the disease.

The concentration of reactive oxygen species may be measured by a variety of methods known in the art. For example, one can determine them from measurements of depletion of anti-oxidative enzymes (glutathione, catalase) in the patient's blood (see Layton et. al.). An alternative is to test the serum of a patient for oxidized low density lipoproteins, using anti-oLDL ELISA immunoassay (see Wilburgur et. al.). One can also measure lipid peroxidation products such as tiabarbituric acid and its derivatives in plasma, or measure arachidonic acid oxidation products in a patient's blood.

The treated blood is administered to the mammal by a method suitable for vaccination selected from the group consisting of intra-arterial injection, intramuscular injection, intravenous injection, subcutaneous injection, intraperitoneal injection, and oral, nasal or rectal administration. Intramuscular injection is preferred.

Ex vivo Treatment of Blood

According to a preferred process of the present invention, an aliquot of blood is extracted from a mammalian subject, preferably a human, and the aliquot of blood is treated ex vivo with certain stressors, described in more detail below. The effect of the stressors is to modify the blood, and/or the cellular or non-cellular fractions thereof, contained in the aliquot. The modified aliquot is then re-introduced into the subject's body by any route suitable for vaccination.

The stressors to which the aliquot of blood is subjected ex vivo according to the method of the present invention are selected from temperature stress (blood temperature above or below body temperature), an oxidative environment and an electromagnetic emission, individually or in any combination, simultaneously or sequentially. Suitably, in human subjects, the aliquot has a volume sufficient that, when re-introduced into the subject's body, at least partial alleviation of the reactive oxygen species mediated disorder is achieved in the subject.

Preferably, the volume of the aliquot is up to about 400 ml, preferably from about 0.1 to about 100 ml, more preferably from about 5 to about 15 ml, even more preferably from about 8 to about 12 ml, and most preferably about 10 ml, along with an anticoagulant, e.g., 2 ml sodium citrate.

It is preferred, according to the invention, to apply all three of the aforementioned stressors simultaneously to the aliquot under treatment, in order to ensure the appropriate modification to the blood. It may also be preferred in some embodiments of the invention to apply any two of the above stressors, for example to apply temperature stress and oxidative stress, temperature stress and an electromagnetic emission, or an electromagnetic emission and oxidative stress. Care must be taken to utilize an appropriate level of the stressors to thereby effectively modify the blood to alleviate the reactive oxygen species mediated disorder in the subject.

The temperature stressor warms the aliquot being treated to a temperature above normal body temperature or cools the aliquot below normal body temperature. The temperature is selected so that the temperature stressor does not cause excessive hemolysis in the blood contained in the aliquot and so that, when the treated aliquot is injected into a subject, alleviation of the reactive oxygen species mediated disorder will be achieved. Preferably, the temperature stressor is applied so that the temperature of all or a part of the aliquot is up to about 55° C., and more preferably in the range of from about −5° C. to about 55° C.

In some preferred embodiments of the invention, the temperature of the aliquot is raised above normal body temperature, such that the mean temperature of the aliquot does not exceed a temperature of about 55° C., more preferably from about 40° C. to about 50° C., even more preferably from about 40° C. to about 44° C., and most preferably about 42.5±1° C.

In other preferred embodiments, the aliquot is cooled below normal body temperature such that the mean temperature of the aliquot is within the range of from about −5° C. to about 36.5° C., more preferably from about 10° C. to about 30° C., and even more preferably from about 15° C. to about 25° C.

The oxidative environment stressor can be the application to the aliquot of solid, liquid or gaseous oxidizing agents.

Preferably, it involves exposing the aliquot to a mixture of medical grade oxygen and ozone gas, most preferably by bubbling through the aliquot, at the aforementioned temperature range, a stream of medical grade oxygen gas having ozone as a minor component therein. The ozone content of the gas stream and the flow rate of the gas stream are preferably selected such that the amount of ozone introduced to the blood aliquot, either on its own or in combination with other stressors, does not give rise to excessive levels of cell damage such that the therapy is rendered ineffective.

Suitably, the gas stream has an ozone content of up to about 300 µg/ml, preferably up to about 100 µg/ml, more preferably about 30 µg/ml, even more preferably up to about 20 µg/ml particularly preferably from about 10 µg/ml to about 20 µg/ml, and most preferably about 14.5±1.0 µg/ml. The gas stream is suitably supplied to the aliquot at a rate of up to about 2.0 liters/min, preferably up to about 0.5 liters/min, more preferably up to about 0.4 liters/min, even more preferably up to about 0.33 liters/min, and most preferably about 0.24±0.024 liters/min, at STP. The lower limit of the flow rate of the gas stream is preferably not lower than 0.01 liters/min, more preferably not lower than 0.1 liters/min, and even more preferably not lower than 0.2 liters/min.

The electromagnetic emission stressor is suitably applied by irradiating the aliquot under treatment from a source of an electromagnetic emission while the aliquot is maintained at the aforementioned temperature and while the oxygen/ozone gaseous mixture is being bubbled through the aliquot. Preferred electromagnetic emissions are selected from photonic radiation, more preferably UV, visible and infrared light, and even more preferably UV light. The most preferred UV sources are UV lamps emitting primarily UV-C band wavelengths, i.e., at wavelengths shorter than about 280 nm. Such lamps may also emit amounts of visible and infrared light. Ultraviolet light corresponding to standard UV-A (wavelengths from about 315 to about 400 nm) and UV-B (wavelengths from about 280 to about 315) sources can also be used. For example, an appropriate dosage of such UV light, applied simultaneously with the aforementioned temperature and oxidative environment stressors, can be obtained from lamps with a combined power output of from about 15 to about 25 watts, arranged to surround the sample container holding the aliquot, each lamp providing an intensity at a distance of one meter, of from about 45–65 mW/cm$^2$. Up to eight such lamps surrounding the sample bottle, with a combined output at 253.7 nm of 15–25 watts, operated at an intensity to deliver a total UV light energy at the surface of the blood of from about 0.025 to about 10 joules/cm$^2$, preferably from about 0.1 to about 3.0 joules/cm$^2$, may advantageously be used. Preferably, four such lamps are used.

The time for which the aliquot is subjected to the stressors is normally within the time range of up to about 60 minutes. The time depends to some extent upon the chosen intensity of the electromagnetic emission, the temperature, the concentration of the oxidizing agent and the rate at which it is supplied to the aliquot. Some experimentation to establish optimum times may be necessary on the part of the operator, once the other stressor levels have been set. Under most stressor conditions, preferred times will be in the approximate range of from about 2 to about 5 minutes, more preferably about 3 or about 3½ minutes. The starting blood temperature, and the rate at which it can be warmed or cooled to a predetermined temperature, tends to vary from subject to subject. Such a treatment provides a modified blood aliquot which is ready for injection into the subject.

In the practice of the preferred process of the present invention, the blood aliquot may be treated with the stressors using an apparatus of the type described in U.S. Pat. No. 4,968,483 to Mueller. The aliquot is placed in a suitable, sterile, UV light-transmissive container, which is fitted into the machine. The UV lamps re switched on for a fixed period before the gas flow is applied to the aliquot providing the oxidative stress, to allow the output of the UV lamps to stabilize. The UV lamps are typically switched on while the temperature of the aliquot is adjusted to the predetermined value, e.g., 42.5±1° C. Then the oxygen/ozone gas mixture, of known composition and controlled flow rate, is applied to the aliquot, for the predetermined duration of up to about 60 minutes, preferably 2 to 5 minutes and most preferably about 3 minutes as discussed above, so that the aliquot experiences all three stressors simultaneously. In this way, blood is appropriately modified according to the present invention to achieve the desired effects.

A subject preferably undergoes a course of treatments, such individual treatment comprising removal of a blood aliquot, treatment thereof as described above and re-administration of the treated aliquot to the subject. A course of such treatments may comprise daily administration of treated blood aliquots for a number of consecutive days, or may comprise a first course of daily treatments for a designated period of time, followed by an interval and then one or more additional courses of daily treatments.

In one preferred embodiment, the subject is given an initial course of treatments comprising the administration of 4 to 6 aliquots of treated blood. In another preferred embodiment, the subject is given an initial course of therapy comprising administration of from 2 to 4 aliquots of treated blood, with the administration of any pair of consecutive aliquots being either on consecutive days, or being separated by a rest period of from 1 to 21 days on which no aliquots are administered to the patient, the rest period separating one selected pair of consecutive aliquots being from about 3 to 15 days. In a more specific, preferred embodiment, the dosage regimen of the initial course of treatments comprises a total of three aliquots, with the first and second aliquots being administered on consecutive days and a rest period of 11 days being provided between the administration of the second and third aliquots.

It may be preferred to subsequently administer additional courses of treatments following the initial course of treatments. Preferably, subsequent courses of treatments are administered at least about three weeks after the end of the initial course of treatments. In one particularly preferred embodiment, the subject receives a second course of treatment comprising the administration of one aliquot of treated blood every 30 days following the end of the initial course of treatments, for a period of 6 months.

It will be appreciated that the spacing between successive courses of treatments should be such that the positive effects of the treatment of the invention are maintained, and may be determined on the basis of the observed response of individual subjects.

EXAMPLES

The invention is demonstrated and illustrated by the following animal experiments, conducted on Wistar rats, according to ethically-approved procedures and protocols.

The experiments investigated the effect of pre-treatment of peripheral blood exposed to immune modulation therapy on LPS-induced impairment of LTP in rat hippocampal tissue. Preliminary studies were also carried out in cortical tissue to explore the consequence of immune modulation therapy on the accumulation of ROS, the concentration of the cytokines TNFα and IL-10, as well as IL-1 receptor type I, and on the activity of the stress-activated protein kinase, JNK.

Experimental Procedure

Animals

Four groups of eight male Wistar rats (300–350 g; BioResources Unit, Trinity College Dublin, Republic of Ireland) were used in these experiments. Animals were housed in groups of four under a 12-hour light schedule, ambient temperature was controlled between 22 and 23° C. and rats were maintained under veterinary supervision.

Treatment Protocol

Whole blood was obtained by cardiac puncture from donor rats and anticoagulated with sodium citrate (10 ml of blood+2 ml of 3.13% sodium citrate solution). The anticoagulated blood was divided into two aliquots; 2 ml to be used for sham treatment and 10 ml to undergo immune modulation treatment. For immune modulation treatment, 10 ml of anticoagulated blood was transferred to a custom-built sterile, low-density polyethylene disposable blood container (Vasogen Inc, Toronto, ON, Canada) and exposed to a combination of controlled physiochemical stress factors in a medical device (Vasogen Inc).

During processing, the temperature of the blood was raised to 42.5° C., during which time blood was exposed to UV light (maximum emission spectrum at 254 nm). When this temperature was reached, a gas mixture of 14.5±1.0 µg/mL of ozone in medical oxygen was bubbled through the blood at a flow rate of 240±24 mL per min for 3 minutes, after which time the heat and UVC light sources were turned off. The foaming action caused by bubbling the gas through the blood increased the surface area exposed to the UVC light. The blood was then allowed to settle to the bottom of the blood container and was then ready to be used. Two groups of 16 rats were treated by intramuscular injection with 150 µL of processed blood or untreated blood (sham treatment). Injections were administered 14 days, 13 days and 1 day before LPS challenge/induction of LTP.

Induction of LTP in Perforant Path-Granule Cell Synapses In Vivo

Rats were anesthetized by intraperitoneal injection of urethane (1.5 g/kg). All rats received LPS (100 µg/kg) or saline, intraperitoneally and monitored for 3 h. A bipolar stimulating electrode and a unipolar recording electrode were placed in the perforant path (4.4 mm lateral to Lambda) and in the dorsal cell body region of the dentate gyrus (2.5 mm lateral and 3.9 mm posterior to Bregma), respectively, and 0.033-Hz test shocks were given for 10 min before, and 40 min after, titanic stimulation (three trains of stimuli delivered at 30-s intervals, 250 Hz for 200 ms (McGahon & Lynch, 1996)). Rats were killed by decapitation; cross-chopped slices (350×350 µm) were prepared from dentate gyri, entorhinal cortex, hippocampus and cortex and used to prepare dissociated cells (see below) or frozen separately in Krebs solution containing 10% dimethyl sulfoxide (Haan & Bowen, 1981) and stored at −80° C. For analysis, slices were thawed rapidly and rinsed in fresh oxygenated Krebs solution before preparation of homogenate or the crude synaptosomal pellet $P_2$ (McGahon & Lynch, 1996).

Analysis of Reactive Oxygen Species Formation

The formation of reactive oxygen species was assessed by analyzing formation of the highly-fluorescent 2′,7-dichlorofluorescein (DCF) from the non-fluorescent probe, 2′,7-dichlorofluorescein diacetate (DCFH-DA; Molecular Probes, USA; LeBel et al., 1992). The synaptosomal pellet, $P_2$, prepared from cortex, was resuspended in 1 mL ice-cold 40 mM Tris buffer (pH 7.4), incubated at 37° C. for 15 min with DCFH-DA (10 µL; final concentration 5 µM; from a stock solution of 500 µM in methanol) and the reaction was terminated by centrifugation at 13,000×g for 8 min at 4° C. Pellets were resuspended in 1.5 mL of ice-cold 40 mM Tris buffer, pH 7.4, and monitored for fluorescence at 37° C. (excitation, 488 nm; emission, 525 nm). Reactive oxygen species formation was quantified from a standard curve of DCF in methanol (range 0 to 5 µM). Protein concentration was determined (Bradford, 1976) and the results were expressed as nmol/mg protein/min.

Analysis of TNFα and IL-10 Concentration

A commercially available Enzyme-linked immunosorbent assay was used to analyze cortical TNFα (Biosource International Inc.) and cortical IL-10 was measured using an IL-10 Cytoset Antibody Pair (Biosource International Inc.). Each tissue was added to 1 mL of Iscove's culture medium containing 5% fetal bovine serum and a cocktail enzyme inhibitor (100 mM amino-n-caproic acid, 10 mM $Na_2EDTA$, 5 mM Benzamidine HCl, 0.2 mM phenylmethylsulfonyl fluoride). Tissue was homogenized and centrifuged at 10,000 rpm at 4° C. for 10 min. Supernatants were removed and analyzed for TNFα using ELISA. Protein concentration was determined (Bradford, 1976) and the results were expressed as pg/mg protein.

Analysis of JNK Activity and IL-1 Receptor Type I Concentration

JNK activity and IL-1 Receptor Type I concentration was analyzed using Western Blotting technique in samples prepared from cortical tissue. Tissue homogenates were diluted to equalize for protein concentration (Bradford, 1976) and 10 µL aliquots (1 mg/mL) were added to 5 µL of sample buffer (0.5 mM Tris-HCl, pH 6.8, 10% glycerol, 10% SDS, 5% b-mercaptoethanol, 0.05% bromophenol blue, w/v) and boiled for 5 min. Samples were frozen until Western Blotting was performed. 10 µL of each sample was loaded onto gels (10% SDS) for each analysis. Proteins were separated by application of a 32-mA constant current for 25–30 min, transferred onto nitrocellulose strips (225 mA for 75 min), and immunoblotted with the appropriate antibody. To assess JNK activity, proteins were immunoblotted with an antibody that specifically targets phosphorylated JNK (Santa Cruz Biotechnology, Inc; 1:100 in TBS and 0.1% Tween 20 containing 1% BSA) for 2 h at room temperature.

IL-1 Receptor Type I concentration was assessed by immunoblotting proteins with a rabbit polyclonal antibody raised against an epitope mapping at the carboxy terminus of IL-1RI of mouse origin (Santa Cruz Biotechnology, Inc.; 1:2000 in PBS and 0.1% Tween 20 containing 2% non-fat dried milk) for 45 min at room temperature and 45 min at 37° C. Nitrocellulose strips were washed and incubated with secondary antibody [peroxide-linked anti-mouse IgG; 1:300 dilution (Sigma) for 2 h at room temperature in the case of JNK and with HRP-linked anti-rabbit antibody; 1:2000 dilution (Amersham, UK) for 60 min at room temperature and 30 min at 37° C. in the case of IL-1 Receptor Type I. Visualization of phosphorylated JNK was achieved using SuperSignal West Dura Extended Duration Substrate (Pierce, USA). Immunoblots were immersed in substrate for 5 min and subsequently exposed to film for 1 s. Protein complexes of IL-1 Receptor Type I were visualized by ECL detection (Amersham, UK) and immunoblots were exposed to film overnight at 4° C. In both cases films were processed using a Fuji x-ray processor. Quantification of protein bands was achieved by densitometric analysis using two software packages, Grab It (Grab It Annotating Grabber, version 2.04.7, Synotics; UVP Ltd) and Gelworks (Gelworks ID, version 2.51; UVP Ltd) for photography and densitometry, respectively. Gelworks provides a single value (in arbitrary units) representing the density of each blot.

Analysis of Glutamate Release

Glutamate release was assessed in the impure synaptosomal preparation, $P_2$, obtained from dentate gyrus; either freshly-prepared tissue was used or alternatively, $P_2$ was prepared from frozen slices of dentate gyri which were obtained from rats in which electrophysiological recordings were made (McGahon and Lynch, 1996). In both cases, $P_2$ preparations were resuspended in oxygenenated Krebs solution containing 2 mM $CaCl_2$ and glutamate release was assessed as described previously (McGahon et al., 1996). Briefly, synaptosomal tissue was aliquotted onto Millipore filters (o45 µm), rinsed under vacuum and the filtrate was discarded. Synaptosomes were then incubated in 250 µl oxygenated Krebs solution at 37° C. for 3 min, in the presence or absence of 40 mM KCl, and filtrate was collected and stored for analysis as described (Ordronneau et al., 1991). In some experiments, synaptosomes were incubated at 37° C. for 20 min in Krebs solution containing IL-1β (1 ng/ml) in the presence or absence of Vasoactive Intestinal Peptide (VIP; 1 µM). Triplicate samples (50 µl) or glutamate standards (50 µl; 25 nM to 1 µM prepared in 100 mM $NaH_2PO_4$ buffer, pH 8.0) were added to glutaraldehyde-coated 96-well plates, incubated for 60 min at 37° C., washed with 100 mM $NaH_2PO_4$ buffer. Ethanolamine (250 µl; 0.1 M in 100 mM $NaH_2PO_4$ 4 buffer) was used to bind unreacted aldehydes and donkey serum (200 µl; 3% in PBS-T) was added to block non-specific binding. Samples were incubated overnight at 4° C. in the presence of anti-glutamate antibody (raised in rabbit; 100 µl; 1:5,000 in PBS-T; Sigma, UK), washed and reacted with secondary antibody (anti-rabbit horseradish peroxidase (HRP)-linked secondary antibody; 100 µl; 1:10,000 in PBS-T; Amersham, UK) for 60 min at room temperature. 3.3', 4.4'-Tetramethylbenzidine liquid substrate was added as chromogen and incubation continued for exactly 60 min at room temperature, at which time the reaction was stopped by $H_2SO_4$ (4 M; 30 µl). Optical densities were determined at 450 mm using a multiwell plate reader and values were calculated with reference to the standard curve, corrected for protein (Bradford, 1976) and expressed as µmol glutamate/mg protein.

Analysis of IL-1β Concentration

IL-1β concentration in hippocampal was analysed by ELISA (R & D Systems, UK). Antibody-coated (100 µl; 1.0 µg/ml final concentration, diluted in phosphate buffered saline (PBS), pH 7.3; goat anti-rat IL-1βantibody) 96=well plates were incubated overnight at room temperature, washed several times with PBS containing 0.05% Tween 20, blocked for 1 hour at room temperature with 300 µl blocking buffer, (PBS, pH 7.3 containing 5% sucrose, 1% bovine serum albumin (BSA), and 0.05% $NaN_3$). After several washes, plates were incubated with IL-1β standards (100 µl; 0–1000 pg/ml in PBS containing 1% BSA) or samples (homogenized in Krebs solution containing 2 mM $CaCl_2$) for 2 hours at room temperature. Samples were incubated with secondary antibody (100 µl; final concentration 350 ng/ml in PBS containing 1% BSA and 2% normal goat serum; biotinylated goat anti-rat IL-1β antibody) for 2 hours at room temperature, washed and incubated in detection agent (100 µl; horseradish peroxidase conjugated streptavidin; 1:200 dilution in PBS containing 1% BSA) for 20 min at room temperature. Substrate solution (100 µl; 1:1 mixture of $H_2O_2$ and tetramethylbenzidine) was added, samples were incubated at room temperature in the dark for 1 hour after which time the reaction was stopped using 50 µl 1 M $H_2SO_4$. Absorbance was read at 450 nm, values were corrected for protein (Bradford, 1976) and expressed as pg IL-1β/mg protein.

TUNEL Staining

Dissociated cells were prepared by enzymatic and mechanical digestion of fresh hippocampal slices. Slices were incubated with collagenase (0.125%) in PBS for 30 min at room temperature, washed with PBS to terminate collagenase digestion, and then gently triturated with a glass Pasteur pipette, before passing through a nylon mesh filter to remove tissue clumps. Cells were than cytospun onto glass microscope slides, fixed with methanol and stored until use.

TUNEL (Terminal deoxynucleotidyl Transferase (TdT)-mediated dUTP Nick-End Labeling) staining, which identifies nuclei with fragmented DNA (a characteristic of apoptotic cells), was performed according to the manufacturer's instructions. Briefly, fixed cytospun cells were washed and permeabilized. Cells were equilibrated in buffer (200 mM potassium cacodylate (pH 6.6 at 25° C.), 25 mM Tris-HCl (pH 5.5 at 25° C.), 0.2 mM DTT, 0.25 mg/ml BSA, 2.5 mM $CoCl_2$) for 5 min at room temperature and incubated in TdT reaction mixture (30 µl; 98 µl equilibration buffer, 1 µl biotinylated nucleotide mix, 1 µl TdT enzyme) at 37° C. for 1 hour. The reaction was terminated by adding 100 µl 2×SCC (1:10; 2×SCC:deionized water), endogenous peroxidases were blocked by incubating with $H_2O_2$ (100 µl; 0.3% in PBS) for 5 min at room temperature, and washed cells were incubated for 30 min at room temperature in streptavidin HRP solution (100 µl; 1:500 in PBS) to allow binding to biotinylated nucleotides. Diaminobenzidine solution was added to washed cells, and the incubation proceeded for 10 min at room temperature. Cells were washed with deionised water, dehydrated through graded ethanol, and then cleared with xylene after which slides were mounted in DPX mounting medium and coverslipped. TUNEL positive cells were expressed as a percentage of the total.

Statistical Analysis

Data were analyzed, as appropriate, using either the Student's t-test for independent means, or by using a one-way analysis of variance (ANOVA) followed by post hoc analysis using the Student Newman Keuls test.

RESULTS

A: Hippocampus

Figure 1A:
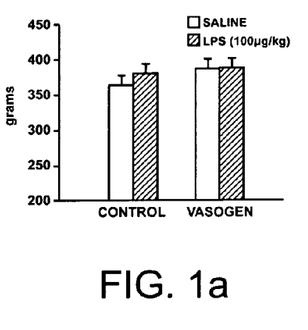
Figure 1B:
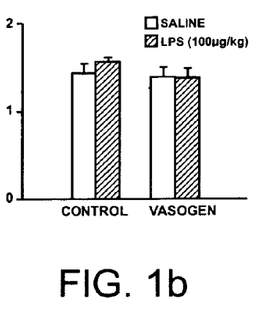
Figure 1C:
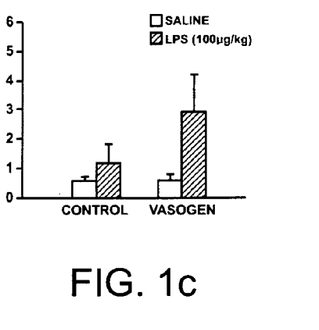
Figure 1D:
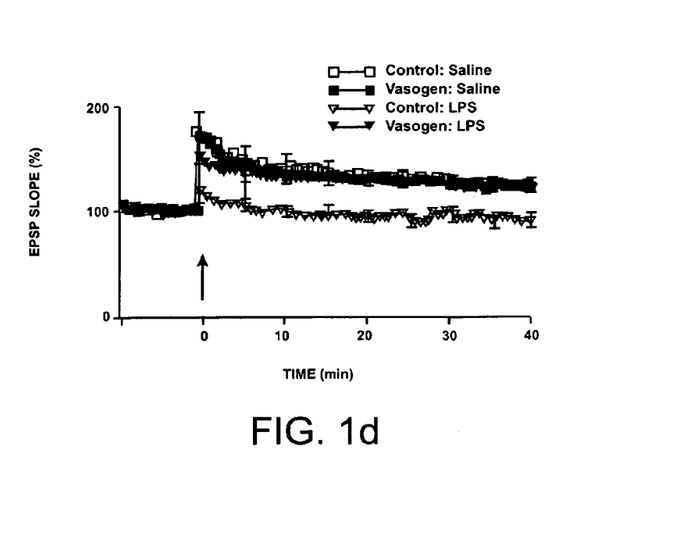
FIG. 1d illustrates a mean pre-tetanus EPSP slope.

Mean body weight, dose of urethane administered to induce anaesthesia, and stimulus strength required to induce an epsp spike were calculated. There was no significant difference between groups in body weight (FIG. 1A) or urethane concentration (FIG. 1B) administered due to immune modulation therapy.

FIG. 1 demonstrates that immune modulation therapy does not significantly alter body weight (a) or dose of urethane administered to induce anaesthesia (b). There is however an increase in the amplitude required to induce an action potential (c). The data are expressed as means with standard errors.

Figure 2:
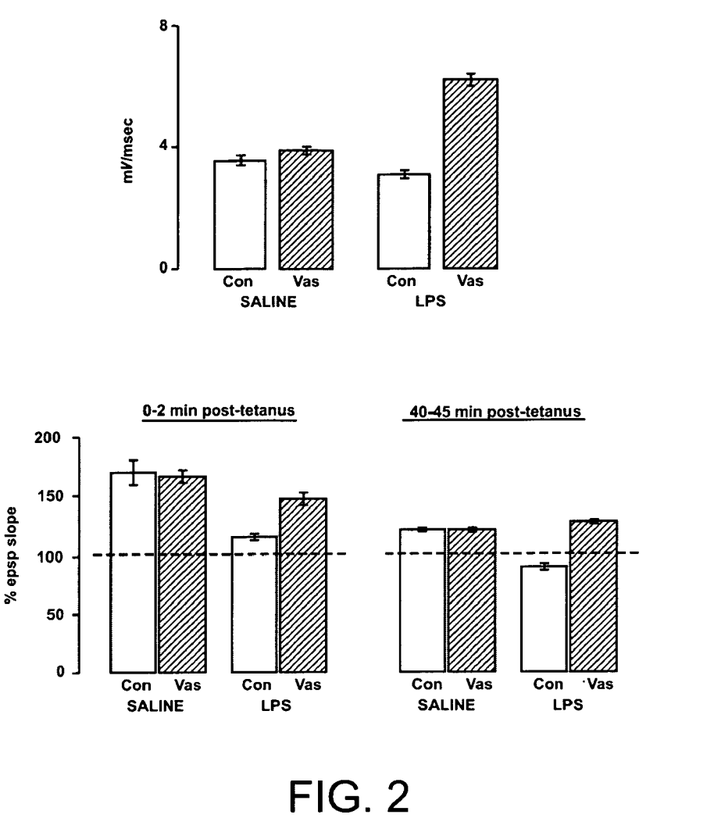
FIG. 2 is a graphical presentation of the results of testing LPS-induced impairment of LTP described in the experimental section below.

Tetanic stimulation delivered to the perforant path 3 h after intraperitoneal injection of LPS resulted in an increase in the mean slope of the population excitatory post-synaptic potential (epsp). The mean percentage change in the 2 min immediately following tetanic stimulation (±SEM; compared with the 5 min immediately before tetanic stimulation) was 114.49 (±2.79), but this was not maintained so that the mean percentage change in population epsp slope in the last 5 min of the experiment was 90.32 (±2.42). The corresponding values in the saline-treated control rats were 170.15 (±10.16) and 121.28 (±1.20), respectively (FIG. 2). The LPS induced inhibition of LTP was blocked by pre-treatment with immune modulation therapy.

FIG. 2 demonstrates that the LPS-induced impairment of LTP, was inhibited by pre-treatment with immune modulation therapy. The mean population epsp slope immediately after tetanic stimulation was attenuated in LPS-treated rats compared with saline-treated rats and was close to baseline at the end of the 40 min post-tetanus recording period. The inhibitory effect of LPS on LTP was blocked by pre-treatment with immune modulation therapy, which exerted no significant effect in saline-challenged rats. The data presented are means of seven to eight observations in each treatment group.

The mean percentage change in population epsp slope (±SEM) in the 2 min immediately after tetanic stimulation was 166.85 (±4.54) in the sham pretreated, saline challenged group compared with 147.44 (±5.84) in the group pretreated with immune modulation therapy and challenged with LPS. In the last 5 min of the experiment the values were 121.96 (±0.85) and 128.07 (±1.46), respectively (n=7–8).

Dissocated cells prepared form fresh hippocampal tissue displayed an increased number of apoptotic cells after LPS injection as evidenced by increased number of cells displaying dark brown stained nuclei i.e. TUNEL positive cells. This contrasts with cells prepared from hippocampus of saline-treated rats and rats treated with immune modulation therapy. Treatment with immune modulation therapy reversed the effects of LPS as shown by a reduction in the number of cells displaying TUNEL positive staining. The precentage of TUNEL positive cells was significantly increased in the LPS-treated group compared with the control treated group (p<0.01; ANOVA) and demonstrates that the immune modulation therapy reversed the degenerative effect of LPS (p<0.01; ANOVA).

B: Cortex

Animals were administered either immune modulation therapy or sham treatments, as previously described, and the following measurements were made in the cortex: ROS accumulation, TNF-α and IL-10 levels. These experiments were performed without LPS stimulation of the animals.

Figure 3:
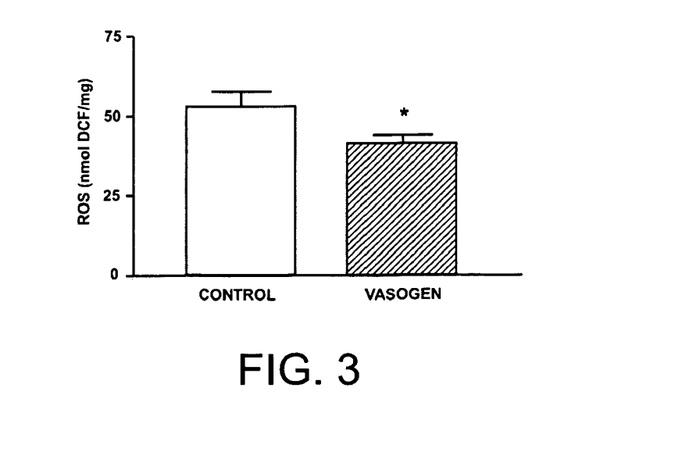
FIG. 3 is a graphical presentation of the measurements of reactive oxygen species accumulation described in the experimental section below. Data is expressed as means with standard errors. The * indicates $p<0.05$ calculated according to the Student t-test for independent means.

FIG. 3 indicates that immune modulation therapy significantly reduces reactive oxygen species accumulation in the cortex (p<0.05; student's t-test for independent means, n=7–8). The data are expressed as means with standard errors.

Figure 4A:
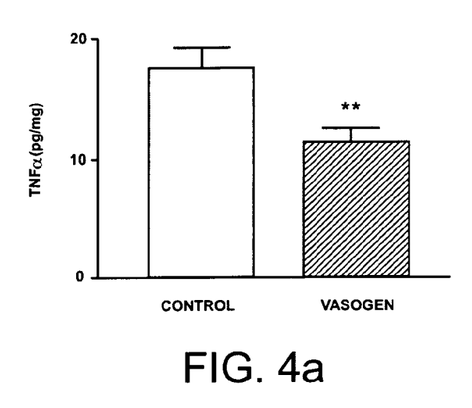
FIG. 4 is a graphic presentation of the inflammatory cytokine $TNF_2$ measurements and anti-inflammatory cytokine IL-10 measurements in the cortex of test animals, described in the experimental section below. Data is expressed as means with standard errors. The ** indicates $p<0.01$ calculated according to the Student t-test for independent means.
Figure 4B:
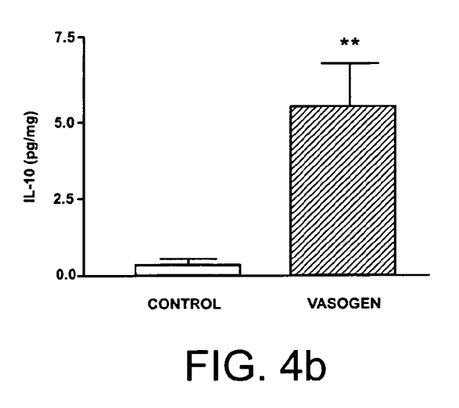

The concentration of pro-inflammatory cytokine, TNFα is significantly reduced in the cortex as a result of immune modulation therapy (p<0.01; student's t-test for independent means, FIG. 4a). In contrast, IL-10 concentration is significantly increased (p<0.01; student's t-test for independent means) (FIG. 4b). FIGS. 4a and 4b show that immune modulation therapy significantly reduces TNFα concentration (a) and significantly increases IL-10 concentration (b) in the cortex (p<0.01; student's t-test for independent means; n=7–8). The data are expressed as means with standard errors.

Figure 5:
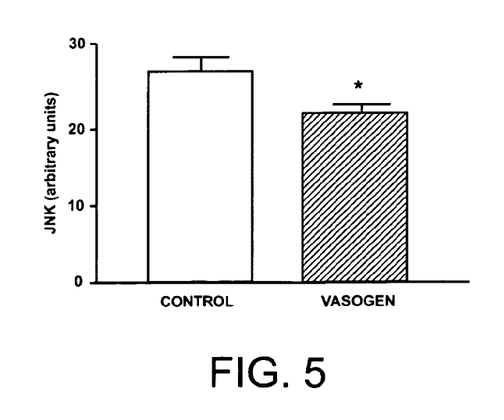
FIG. 5 is a graphical presentation of the measurements of c-Jun $NH_2$-terminal kinase (JNK) activity in the cortex of experimental animals treated as described in the experimental section below. Data is expressed as means with standard errors. The * indicates $p<0.05$ calculated according to the Student t-test for independent means.

FIG. 5 illustrates that immune modulation therapy decreased JNK activity as indicated by a decrease in the phosphorylated form of JNK. Analysis of the mean data obtained from densitometric analysis indicated that Vaso-Care™ therapy significantly reduced kinase activity (p<0.05; student's t-test for independent means). FIG. 5 shows that immune modulation therapy significantly reduces JNK activity in the cortex (p<0.05; student's t-test for independent means; n=7–8). The data are expressed as means with standard errors.

Figure 6:
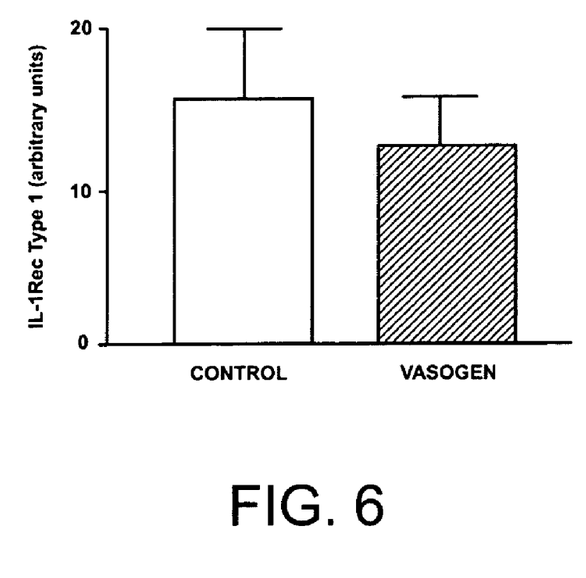
FIG. 6 is a graphical presentation of the results of measurements of IL-1 Receptor Type 1 concentration in cortical tissue of test animals treated as described in the experimental section below. Data is expressed as means with standard errors.

With respect to the concentration of IL-1 Receptor Type I in cortical tissue, pilot work indicates that immune modulation therapy reduces IL-1 Receptor Type I expression (FIG. 6). The concentration of ligand pro-inflammatory IL-1β itself is expected to be lower, and is under examination. FIG. 6 shows that immune modulation therapy reduces the concentration of IL-1 Receptor Type I (preliminary data; n=3). The data are expressed as means with standard errors.

Analysis of endogenous glutamate release in synatosomes prepared from tetanized and untetanized tissue obtained from these rats revealed a significant effect of LPS injection. Addition of 40 mM KCl to synaptosomes prepared from untetanized dentate gyrus obtained from saline-treated control rats, significantly increased glutamate release (p<0.05; Student t-test for paired means) albeit to an attenuated degree. This immune modulation therapy reversed the LPS-induced blockage of KCl stimulated glutamate release in untetanized dentate gyrus and to a more significant degree in tetanized tissue (p<0.01; Student t-test for paired means). This immune modulation therapy may exert its protective effect on syncystic function by acting to prevent this LPS-induced signaling event.

BIBLIOGRAPHY

Bliss T V, Collingridge G L. A synaptic model of memory: long-term potentiation in the hippocampus. Nature. 1993 361(6407):31–9.

Bradford M M. A rapid and sensitive method for the quantitation of microgram quantities of protein utilizing the principle of protein-dye binding. Anal Biochem. 1976 72:248–54.

Green L N. Corticosteroids in the treatment of Sydenham's chorea. Arch. Neurol. January 1978; 35(1): 53–4.

Haan E A, Bowen D M. Protection of neocortical tissue prisms from freeze-thaw injury by dimethyl sulphoxide. J Neurochem. 1981 37(1):243–6.

Kedziora J, Bartosz G. Down's syndrome: a pathology involving the lack of balance of reactive oxygen species. Free Radic. Biol. Med., 1988; 4(5): 317–30.

Kouamé N, Carioto S, Hamet P, Tremblay J. Vasocare-therapy attenuates telemetered temperature response to stress in SHR. 9$^{th}$ International Symposium on SHR and Cardiovascular Genetics, Montreal, Canada, #P-136, Nov. 13–16, 1997.

Layton M E, Pazdernik T L. Reactive oxidant species in piriform cortex extracellular fluid during seizures induced by systemic kainic acid in rats. J. Mol. Neurosci August-October 1999; 13(1–2): 63–8.

LeBel C P, Ischiropoulos H, Bondy S C. Evaluation of the probe 2',7'-dichlorofluorescin as an indicator of reactive oxygen species formation and oxidative stress. Chem Res Toxicol. 1992 5(2):227–31.

Maroney A C, Glicksman M A, Basma A N, Walton K M, Knight E, Murphy C A, Bartlett B A, Finn J P, Angeles T, Matsuda Y, Neff N T, Dionne C A. Motoneuron apoptosis is blocked by CEP-1347 (KT 7515), a novel inhibitor of the JNK signaling pathway. J Neurosci. 1998 18(1): 104–11.

Martin D S D, Towey M, Horrobin D F, Lynch M A. A diet enriched in a-lipoic acid reverses the age-related compromise in antioxidant defenses in rat cortical tissue. Nutritional Neuroscience 2000 3: 193–206.

McGahon B, Lynch M A. The synergism between metabotropic glutamate receptor activation and arachidonic acid on glutamate release is occluded by induction of long-term potentiation in the dentate gyrus. Neuroscience. 1996 72(3):847–55.

Mogi M, Harada M, Narabayashi H, Inagaki H, Minami M, Nagatsu T. Interleukin (IL)-1b, IL-2, IL-4, IL-6 and transforming growth factor-a levels are elevated in ventricular cerebrospinal fluid in juvenile parkinsonism and Parkinson's disease. Neurosci Lett. 1996 211(1):13–6.

Murray C A, Lynch M A. Evidence that increased hippocampal expression of the cytokine interleukin-1b is a common trigger for age- and stress-induced impairments in long-term potentiation. J Neurosci. 1998 18(8):2974–81.

O'Donnell E, Vereker E, Lynch M A. Age-related impairment in LTP is accompanied by enhanced activity of stress-activated protein kinases: analysis of underlying mechanisms. Eur J Neurosci. 2000 12(1):345–52.

Park D S, Stefanis L, Yan C Y, Farinelli S E, Greene L A. Ordering the cell death pathway. Differential effects of BCL2, an interleukin-1-converting enzyme family protease inhibitor, and other survival agents on JNK activation in serum/nerve growth factor-deprived PC12 cells. J Biol Chem. 1996 271(36):21898–905.

Rabinovitch B A, Matukas L, Raju K, Punhani T, deVeber G, Keystone E. VasoCare™ PSCT normalizes the Th2 cell subset in scleroderma. XII Pan-American Congress of Rheumatology, Montreal, Canada, 1998.

Schuchmann S, Heinemann U. Increased mitochondrial superoxide generation in neurons from trisomy 16 mice: a model of Down's syndrome. Free Radic. Biol. Med Jan. 15, 2000; 28(2): 235–50.

Shivji G M, Suzuki H, Mandel A S, Bolton A E, Sauder D N. The effect of VAS972 on allergic contact hypersensitivity J Cutan Med Surg. 2000 4(3):132–7.

Tenneti L, D'Emilia D M, Troy C M, Lipton S A. Role of caspases in N-methyl-D-aspartate-induced apoptosis in cerebrocortical neurons. J Neurochem. 1998 71(3):946–59.

Trembovler V, Beit-Yannai E, Younis F, Gallily R, Horowitz M, Shohami E. Antioxidants attenuate acute toxicity of tumor necrosis factor-alpha induced by brain injury in rat. J. Interferon Cytokine Res July 1999; 19(7): 791–5.

Vereker E, Campbell V, Roche E, McEntee E, Lynch M A. Lipopolysaccharide inhibits long term potentiation in the rat dentate gyrus by activating caspase-1. J Biol Chem. 2000a 275(34):26252–8.

Vereker E, O'Donnell E, Lynch M A. The inhibitory effect of interleukin-1b on long-term potentiation is coupled with increased activity of stress-activated protein kinases. J Neurosci. 2000b 20(18):6811–9.

Wildburger R, Borovic S, Zarkovic N, and Tatzber F. Post-traumatic dynamic changes in the antibody titer against oxidized low density lipoproteins. Wien Klin Wochenshr Sep. 29, 2000; 112(18) 798–803.

What is claimed is:

1. A method for inhibiting the production of reactive oxygen species in a mammalian patient produced by neurological diseases selected from the group consisting of Down's syndrome, Huntington's disease, brain trauma and epilepsy, chronic inflammatory demyelinating polyneuropathy, Guillain-Barré syndrome, myasthenia gravis, dermatomyositis, polymyositis, inclusion body myositis, post stroke, neurosarcoidosis, vascular dementia, closed head trauma, vasospasm, subarachnoid hemorrhage, adrenal leukocytic dystrophy, inclusion body dermatomysitis, minimal cognitive impairment and duchenne muscular dystrophy, which method comprises:

administering to said patient an aliquot of blood which has been treated ex vivo with at least two stressors selected from the group consisting of an oxidative environment, thermal stress and electromagnetic radiation;

wherein the concentration of the reactive oxygen species in said patient is reduced.

2. The method of claim 1, wherein the oxidative environment comprises applying an oxidizing agent to the aliquot.

3. The method of claim 2, wherein the oxidative environment comprises a mixture of ozone gas and medical grade oxygen, the ozone gas being contained in the mixture in a concentration of up to about 300 μg/ml.

4. The method of claim 3, wherein the ozone gas is contained in the mixture in a concentration of up to about 30 μg/ml.

5. The method of claim 4, wherein the ozone gas being contained in the mixture in a concentration of from about 13.5 μg/ml to about 15.5 μg/ml.

6. The method of claim 3, wherein the mixture is applied to the aliquot at a flow rate of up to about 0.33 liters/mm.

7. The method of claim 6, wherein the mixture is applied to the aliquot at a flow rate of from about 0.21 liters/mm to about 0.27 liters/mm.

8. The method of claim 1, wherein the electromagnetic radiation comprises ultraviolet light having one or more UV-C band wavelengths.

9. The method of claim 1, wherein the thermal stressor is applied so that the temperature of at least part of the aliquot is in the range of from about −5° C. to about 55° C.

10. The method of claim 1, wherein the thermal stressor provides for a mean temperature of the blood in the aliquot in the range of from about 37° C. to about 44° C.

11. The method of claim 1, wherein the thermal stressor provides for a mean temperature of the blood in the aliquot in the range of from about 0° C. to about 36.5° C.

12. The method of claim 1, wherein the thermal stressor provides for a mean temperature of the blood in the aliquot in the range of from about 10° C. to about 30° C.

13. The method of claim 1, wherein the thermal stressor provides for a temperature in the range of from about 37° C. to about 55° C.

14. The method of claim 13, wherein the temperature is 42.5±1° C.

15. The method of claim 1, wherein the aliquot has a volume of up to about 400 ml.

16. The method of claim 15, wherein the volume of the aliquot is about 10 ml.

17. The method of claim 16, wherein the volume of the aliquot is about 2 ml.

18. The method of claim 1, wherein the aliquot is subjected to the stressors for a period of up to about 60 minutes.

19. The method of claim 18, wherein the aliquot is subjected to the stressors for a period of about 3 minutes.

20. The method of claim 1, wherein the blood is administered to the mammal by a method suitable for vaccination selected from the group consisting of intra-arterial injection, intramuscular injection, intravenous injection, subcutaneous injection, intraperitoneal injection, and oral, nasal or rectal administration.

21. The method of claim 1, wherein all of the stressors are simultaneously administered to the aliquot.

22. The method of claim 21, wherein the mammal is a human.

23. The method of claim 1, wherein the neurological disease is minimal cognitive impairment.

24. The method of claim 1, wherein the neurological disease is post stroke.

25. The method of claim 1, wherein the neurological disease is vascular dementia.

26. The method of claim 1, wherein the neurological disease is chronic inflammatory demyelinating polyneuropathy.

27. The method of claim 1, wherein the neurological disease is Guillain-Barré syndrome.

28. The method of claim 1, wherein the neurological disease is brain trauma and epilepsy.

* * * * *

UNITED STATES PATENT AND TRADEMARK OFFICE
CERTIFICATE OF CORRECTION

PATENT NO. : 7,122,208 B2 Page 1 of 1
APPLICATION NO. : 10/115943
DATED : October 17, 2006
INVENTOR(S) : Anthony E. Bolton and Arkady Mandel It is certified that error appears in the above-identified patent and that said Letters Patent is hereby corrected as shown below:

On The Title Page Item (54):

Replace "COMPOSITIONS CONTAINING APOPTOTIC ENTITIES"

with

--METHODS FOR TREATING THE INFLAMMATORY COMPONENT OF A BRAIN DISORDER--

At COLUMN 1, LINES 1-2:

Replace "COMPOSITIONS CONTAINING APOPTOTIC ENTITIES"

with

--METHODS FOR TREATING THE INFLAMMATORY COMPONENT OF A BRAIN DISORDER--

Signed and Sealed this

Seventeenth Day of July, 2007

JON W. DUDAS
*Director of the United States Patent and Trademark Office*